(12) United States Patent
Chimenti et al.

(10) Patent No.: US 9,999,738 B2
(45) Date of Patent: Jun. 19, 2018

(54) GEL CUSHION PAD FOR MASK

(75) Inventors: Jeffrey P. Chimenti, South San Francisco, CA (US); Anthony J. Santella, Novato, CA (US)

(73) Assignee: ResMed Limited, Bella Vista (AU)

( * ) Notice: Subject to any disclaimer, the term of this patent is extended or adjusted under 35 U.S.C. 154(b) by 770 days.

(21) Appl. No.: 12/504,512

(22) Filed: Jul. 16, 2009

(65) Prior Publication Data
US 2010/0018535 A1    Jan. 28, 2010

Related U.S. Application Data

(60) Provisional application No. 61/083,480, filed on Jul. 24, 2008.

(51) Int. Cl.
*A62B 18/08*    (2006.01)
*A61M 16/06*    (2006.01)

(52) U.S. Cl.
CPC ........ *A61M 16/06* (2013.01); *A61M 16/0605* (2014.02); *A61M 16/0633* (2014.02); *A61M 16/0683* (2013.01); *A61M 2016/0661* (2013.01)

(58) Field of Classification Search
USPC ............ 128/206.24, 206.23, 203.13, 206.12, 128/206.14, 207.13, 112.1, 889, 894, 128/201.17, 201.19, 201.24, 203.29, 128/205.25; 2/9
See application file for complete search history.

(56) References Cited

U.S. PATENT DOCUMENTS

| | | | |
|---|---|---|---|
| 1,043,649 A * | 11/1912 | Wendell | ................................. 2/9 |
| 2,001,862 A * | 5/1935 | Battey | ....................... 606/204.35 |
| 2,197,973 A * | 4/1940 | Everett et al. | ....................... 2/13 |
| 3,357,426 A | 12/1967 | Cohen | |
| 3,594,813 A * | 7/1971 | Sanderson | ............................ 2/9 |
| 3,682,171 A | 8/1972 | Dali et al. | |
| 3,972,321 A | 8/1976 | Proctor | |
| 4,006,744 A | 2/1977 | Steer | |
| 4,142,527 A | 3/1979 | Garcia | |
| 4,153,051 A * | 5/1979 | Shippert | ......................... 602/17 |
| 4,274,402 A | 6/1981 | Shippert | |

(Continued)

FOREIGN PATENT DOCUMENTS

DE    197 03 526 A1    8/1998
EP    0 466 960 A1    1/1992
(Continued)

OTHER PUBLICATIONS

Adam J. Singer MD et al., "The Cyanoacrylate Topical Skin Adhesives," American Journal of Emergency Medicine, vol. 26, 2008, pp. 490-496.

(Continued)

*Primary Examiner* — Loan H Thanh
*Assistant Examiner* — Shila Jalalzadeh Abyan
(74) *Attorney, Agent, or Firm* — Nixon & Vanderhye P.C.

(57) ABSTRACT

The present invention is a gel cushion that is placed on a user's nose bridge before putting on a ventilator mask. The gel cushion is composed of a tacky gel material, such as a viscoelastic polymer gel. The gel cushion is wider than the edges of the ventilator mask and remains in place even if the mask is repositioned. The gel cushion adapts to the user's face in the area on and around the nose bridge to cushion and seal the ventilator mask in that area.

43 Claims, 3 Drawing Sheets

(56) References Cited

U.S. PATENT DOCUMENTS

| | | | |
|---|---|---|---|
| 4,548,200 A | 10/1985 | Wapner | |
| 4,711,636 A | 12/1987 | Bierman | |
| 4,767,411 A | 8/1988 | Edmunds | |
| 4,790,829 A | 12/1988 | Bowden et al. | |
| 4,802,857 A | 2/1989 | Laughlin | |
| 4,838,878 A | 6/1989 | Kalt et al. | |
| 4,867,146 A * | 9/1989 | Krupnick | A61F 9/00 128/858 |
| 4,919,654 A | 4/1990 | Kalt | |
| 4,966,590 A | 10/1990 | Kalt | |
| 4,969,880 A | 11/1990 | Zamierowski | |
| 4,976,698 A | 12/1990 | Stokley | |
| 5,117,818 A | 6/1992 | Palfy | |
| 5,243,971 A | 9/1993 | Sullivan et al. | |
| 5,261,893 A | 11/1993 | Zamierowski | |
| 5,263,939 A | 11/1993 | Wortrich | |
| 5,304,146 A | 4/1994 | Johnson et al. | |
| 5,364,367 A | 11/1994 | Banks et al. | |
| 5,438,710 A | 8/1995 | McDonald et al. | |
| 5,513,635 A | 5/1996 | Bedi | |
| 5,662,101 A * | 9/1997 | Ogden et al. | 128/205.25 |
| 5,682,881 A | 11/1997 | Winthrop et al. | |
| 5,707,342 A | 1/1998 | Tanaka | |
| 5,727,544 A * | 3/1998 | Miura | A41D 13/11 128/201.13 |
| 5,735,272 A | 4/1998 | Dillon et al. | |
| 5,752,511 A | 5/1998 | Simmons et al. | |
| 5,807,341 A | 9/1998 | Heim | |
| 5,842,469 A | 12/1998 | Rapp et al. | |
| 5,884,624 A | 3/1999 | Barnett et al. | |
| 5,918,598 A | 7/1999 | Belfer et al. | |
| 6,026,811 A | 2/2000 | Settle | |
| 6,029,658 A * | 2/2000 | De Voss | A61F 5/08 128/200.24 |
| 6,092,521 A * | 7/2000 | Miura | 128/201.13 |
| 6,095,996 A | 8/2000 | Steer et al. | |
| 6,119,694 A | 9/2000 | Correa et al. | |
| 6,211,263 B1 | 4/2001 | Cinelli et al. | |
| 6,231,548 B1 | 5/2001 | Bassett | |
| 6,258,066 B1 | 7/2001 | Urich | |
| 6,328,038 B1 | 12/2001 | Kessler et al. | |
| 6,338,340 B1 | 1/2002 | Finch et al. | |
| 6,341,606 B1 | 1/2002 | Bordewick et al. | |
| 6,358,279 B1 | 3/2002 | Tahi et al. | |
| 6,419,660 B1 | 7/2002 | Russo | |
| 6,423,036 B1 | 7/2002 | Van Huizen | |
| 6,434,796 B1 | 8/2002 | Speirs | |
| 6,448,303 B1 | 9/2002 | Paul | |
| 6,482,178 B1 | 11/2002 | Andrews et al. | |
| 6,533,410 B1 | 3/2003 | Shefler et al. | |
| 6,561,192 B2 | 5/2003 | Palmer | |
| 6,579,267 B2 | 6/2003 | Lynch et al. | |
| 6,607,516 B2 | 8/2003 | Cinelli et al. | |
| 6,663,600 B2 | 12/2003 | Bierman et al. | |
| 6,669,712 B1 | 12/2003 | Cardoso | |
| 6,701,927 B2 * | 3/2004 | Kwok et al. | 128/207.13 |
| 6,710,099 B2 | 3/2004 | Cinelli et al. | |
| 6,972,003 B2 | 12/2005 | Bierman et al. | |
| 7,018,362 B2 | 3/2006 | Bierman et al. | |
| 7,076,282 B2 | 7/2006 | Munro et al. | |
| 7,146,976 B2 | 12/2006 | McKown | |
| 7,152,601 B2 | 12/2006 | Barakat et al. | |
| 7,207,328 B1 | 4/2007 | Altemus | |
| 7,243,649 B2 * | 7/2007 | Moenning | A61M 16/06 128/203.12 |
| D552,733 S | 10/2007 | Criscuolo et al. | |
| 8,365,733 B2 * | 2/2013 | Rutan | 128/206.24 |
| 2002/0066452 A1 | 6/2002 | Kessler et al. | |
| 2002/0143296 A1 | 10/2002 | Russo | |
| 2002/0157673 A1 | 10/2002 | Kessler et al. | |
| 2002/0185134 A1 | 12/2002 | Bishop | |
| 2003/0019495 A1 * | 1/2003 | Palkon et al. | 128/206.21 |
| 2003/0023182 A1 | 1/2003 | Mault et al. | |
| 2004/0106891 A1 | 6/2004 | Langan et al. | |
| 2004/0111104 A1 | 6/2004 | Schein et al. | |
| 2004/0112387 A1 * | 6/2004 | Lang et al. | 128/206.24 |
| 2004/0118406 A1 * | 6/2004 | Lithgow et al. | 128/206.24 |
| 2004/0118412 A1 * | 6/2004 | Piletti-Reyes | 128/876 |
| 2004/0127856 A1 | 7/2004 | Johnson | |
| 2004/0226564 A1 | 11/2004 | Persson | |
| 2005/0051171 A1 | 3/2005 | Booth | |
| 2005/0100566 A1 * | 5/2005 | Morikane | A61K 8/0208 424/401 |
| 2005/0101933 A1 | 5/2005 | Marrs et al. | |
| 2006/0095008 A1 | 5/2006 | Lampropoulos et al. | |
| 2006/0095009 A1 | 5/2006 | Lampropoulos et al. | |
| 2007/0157934 A1 * | 7/2007 | Lang | A61M 16/06 128/207.11 |
| 2007/0163594 A1 | 7/2007 | Ho et al. | |
| 2007/0215161 A1 * | 9/2007 | Frater et al. | 128/206.24 |
| 2007/0221219 A1 | 9/2007 | Christy et al. | |
| 2007/0282272 A1 | 12/2007 | Bannon et al. | |
| 2008/0004573 A1 | 1/2008 | Kaufmann et al. | |
| 2008/0065022 A1 | 3/2008 | Kyvik et al. | |
| 2008/0110469 A1 | 5/2008 | Weinberg | |
| 2008/0141437 A1 * | 6/2008 | Braunecker et al. | 2/206 |
| 2008/0149104 A1 * | 6/2008 | Eifler | 128/206.24 |
| 2008/0200880 A1 | 8/2008 | Kyvik et al. | |
| 2009/0107507 A1 | 4/2009 | Moore | |
| 2009/0114228 A1 * | 5/2009 | Kirschner | 128/206.13 |
| 2009/0139525 A1 | 6/2009 | Schirm | |
| 2009/0187130 A1 * | 7/2009 | Asmus | A61L 15/46 602/57 |
| 2009/0223522 A1 * | 9/2009 | Hernandez | A61M 16/06 128/206.26 |
| 2010/0000534 A1 | 1/2010 | Kooij et al. | |
| 2010/0018535 A1 | 1/2010 | Chimenti et al. | |
| 2010/0031958 A1 | 2/2010 | Stewart | |
| 2010/0258136 A1 | 10/2010 | Doherty et al. | |
| 2011/0005524 A1 * | 1/2011 | Veliss | A61M 16/0666 128/206.24 |
| 2012/0073576 A1 * | 3/2012 | Wondka | 128/205.25 |

FOREIGN PATENT DOCUMENTS

| | | | |
|---|---|---|---|
| EP | 0776679 A1 * | 1/1995 | |
| EP | 0 776 679 A1 | 6/1997 | |
| EP | 776679 A1 * | 6/1997 | A62B 9/00 |
| WO | WO 98/23305 A1 | 6/1998 | |
| WO | WO 99/16327 A1 | 4/1999 | |
| WO | WO 99/25410 A1 | 5/1999 | |
| WO | WO 00/50121 A1 | 8/2000 | |
| WO | WO 02/38221 A1 | 5/2002 | |
| WO | WO 2007/143772 A2 | 12/2007 | |
| WO | WO 2009/146313 A1 | 12/2009 | |
| WO | WO 2010/011575 A1 | 1/2010 | |

OTHER PUBLICATIONS

Subbu Venkatraman et al., "Review Skin Adhesives and Skin Adhesion 1. Transdermal Drug Delivery Systems," Biomaterials, vol. 19, 1998, pp. 1119-1136.

Hans Rudolph, Inc., "A New Nasal CPAP/Bilevel Mask", 1 page.

GaleMed Corporation Components Supply Brochure, 30 pages.

Joel W. Beam, "Tissue Adhesives for Simple Traumatic Lacerations," Journal of Athletic Training, 2008, vol. 43, No. 2, pp. 222-224.

Extended European Search Report dated Sep. 3, 2009 in corresponding EP Application No. 09161984.1.

Kooij et al., U.S. Appl. No. 61/080,847, filed Jul. 15, 2008.

Extended European Search Report dated Nov. 14, 2017 issued in European Application No. 09800832.9 (8 pages).

\* cited by examiner

GEL CUSHION PAD FOR MASK

RELATED APPLICATION

This application claims priority from U.S. Provisional Application No. 61/083,480, filed Jul. 24, 2008, entitled GEL CUSHION FOR MASK, and invented by Jeffrey P. Chimenti and Anthony J. Santella. This prior application is expressly incorporated herein by reference.

BACKGROUND OF THE INVENTION

Field of the Invention

The invention is in the field of cushions for ventilator masks. The invention is a cushion pad composed of a tacky gel material that is placed on a user's face, covering the nose bridge area, before putting on a ventilator mask.

Description of the Relevant Art

Sleep Apnea is a condition in which the airway is obstructed during sleep, resulting in reduced oxygen flow and difficulties in maintaining deeper levels of sleep. Sleep apnea is typically treated by providing a pressurized flow of air using a Continuous Positive Airway Pressure ("CPAP") or similar machine. Pressurized air is supplied to a ventilator mask that fits over the user's nose (nasal mask) or nose and mouth (full face mask). Since the air inside the mask is pressurized, the mask must fit tightly to the user's face to be effective. This treatment for sleep apnea requires the user to wear the mask while sleeping for several hours at a time. Ventilation masks are also used in other situations, not involving sleep apnea, for breathing assistance.

Wearing a ventilation mask for an extended time can cause skin irritation and even bruising of the face, especially at the bridge of the nose. While most ventilation masks have a cushion around the areas that contact the user's face, such cushions are not completely effective.

Another factor in user comfort is the quality of the fit between a ventilator mask and the user's face. Although faces are widely varied in shapes and sizes, ventilation masks are typically made in a few standard shapes and sizes. The standard mask shapes and sizes may work fine with some faces, but may not conform closely to all faces of actual users, particularly in the nose bridge area. Where a ventilation mask does not fit well, the straps that hold the mask may need to be tightened to create an effective seal, but at the expense of significant discomfort.

SUMMARY OF THE INVENTION

The present invention is a gel cushion that is placed on a user's nose bridge before putting on a ventilator mask. The gel cushion is composed of a tacky gel material, such as a viscoelastic polymer gel. The gel cushion is wider than the edges of the ventilator mask and remains in place even if the mask is repositioned. The gel cushion adapts to the user's face in the area around the nose bridge to cushion and seal the ventilator mask.

More specifically, the cushion pad is separate from the ventilator mask. It has a central lobe and two side lobes. The central lobe extends upward from a user's nose and the side lobes extend laterally from the user's nose. The cushion pad is used by placing it on the nose bridge of the user and positioning the central lobe to extend upward from the user's nose and the side lobe to extend laterally from the user's nose. After the cushion pad is in position, a ventilator mask is placed on the cushion pad so that the cushion pad is positioned between the user's nose bridge and the ventilator mask. The cushion pad may be included in a kit with an additional pad or pads in a sealable container.

The features and advantages described in the specification are not all inclusive, and particularly, many additional features and advantages will be apparent to one of ordinary skill in the art in view of the drawings, specification and claims hereof. Moreover, it should be noted that the language used in the specification has been principally selected for readability and instructional purposes, and may not have been selected to delineate or circumscribe the inventive subject matter, resort to the claims being necessary to determine such inventive subject matter.

DETAILED DESCRIPTION OF THE PREFERRED EMBODIMENTS

The drawings depict various preferred embodiments of the present invention for purposes of illustration only. One skilled in the art will readily recognize from the following discussion that alternative embodiments of the structures and methods illustrated herein may be employed without departing from the principles of the invention described herein.

The present invention relates to an improvement in ventilator masks. More specifically, the invention is a cushion composed of a tacky gel material that is placed on the user's nose bridge before a ventilator mask is put on. The gel cushion fits between the user's face and the ventilator mask to cushion the mask to avoid skin irritation and bruising from the mask. The gel cushion invention is intended to protect and cushion the nose bridge of the user and to seal the ventilation mask in that area.

Figure 1A:
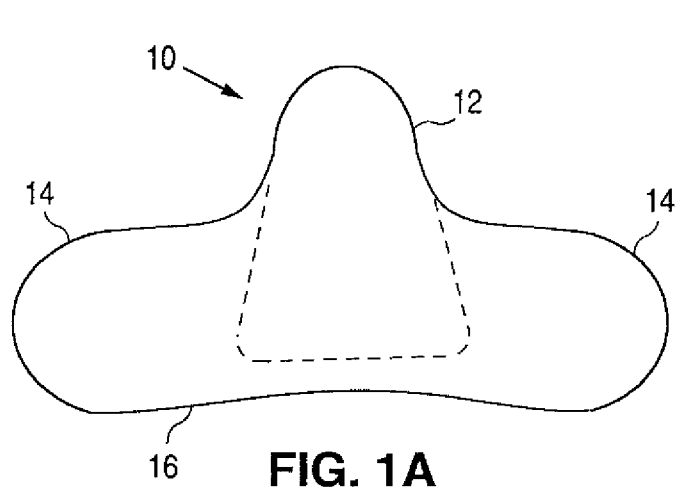
FIGS. 1a, 1b, and 1c are plan, bottom-edge, and side-edge views, respectively, of a gel cushion of the present invention.
Figure 1C:
Figure 1B:
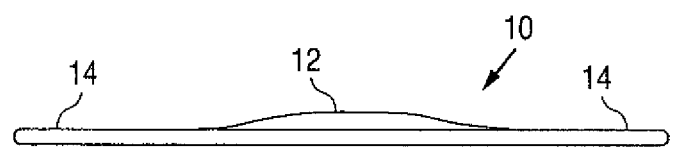

The gel cushion of the present invention is shown in plan, bottom-edge and side-edge views in FIGS. 1a-1c. The gel cushion 10 has a central region or lobe 12 and two side flaps or lobes 14. The central lobe 12 is thickest at the top, about 3/16 of an inch thick, and tapers down to about 1/8 of an inch thick at the side lobes 14. The central lobe 12 of the gel cushion 10 absorbs the pressure of the ventilator mask on the user's nose bridge. The side lobes 14 provide a transition from the thicker central lobe. The lower edge 16 of the cushion is further tapered to avoid undue leakage where the cushion ends.

Figure 2A:
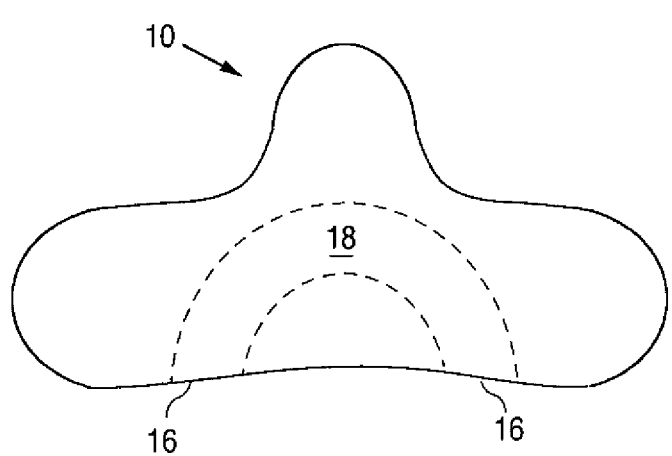
FIGS. 2a and 2b are plan and side-edge views, respectively, of another embodiment of a gel cushion of the present invention.

FIG. 2a shows a semi-annular region 18, which is the region in which a typical ventilator mask contacts the gel cushion. Once the gel cushion 10 is placed on the user's nose bridge, a ventilator mask is put on. The precise contours of the mask are not critical because the gel cushion 10 covers the entire nose bridge area and will cushion and seal the mask wherever it is placed. The mask can be repositioned without moving the gel cushion, which reduces the stress on the user's nose bridge.

Figure 2B:

FIGS. 2a and 2b show an alternative embodiment of the gel cushion invention. The gel cushion shown in FIGS. 2a-2b has a uniform thickness of about ⅛ inch, instead of a thicker central lobe 12 (FIG. 1a). Again the lower edge 16 is tapered to prevent leakage at the bottom of the gel cushion.

The material of the gel cushion is a soft, gel material, preferably a viscoelastic-polymeric gel. Other materials that can be used include thermoplastic elastomer, styrenic block copolymer, polyolefin blend, elastomeric alloy, thermoplastic polyurethane, thermoplastic copolyester, or thermoplastic polyamide. The gel material must be hypoallergenic so that it will not cause irritation of the user's skin. It should also be silicone- and latex-free. Viscoelastic polymer gel is preferably made with a USP medical grade mineral oil. The material of the gel cushion can be provided in a variety of colors, and can be scented for aromatherapy. The preferred viscoelastic-polymeric gel material has a hardness of about 48 on the 000 or Shore A scales.

The gel material is preferably a thermoplastic, so it can be melted and cast or molded to the desired shape. One preferred method of making the gel cushion is to pour molten material into an open mold and remove the gel cushion after it solidifies. The gel material should be somewhat tacky so that it stays on the user's nose bridge during use and when the ventilator mask is put on and taken off or its position is shifted. Tackiness is related to the temperature of molten material before casting, and it has been observed that a higher temperature provides more tack in the gel cushion. The desired temperature of the preferred viscoelastic-polymeric gel is in the range of about 375 to 400° F. (about 190 to 205° C.) in its molten state prior to casting.

In the case of the uniform thickness gel cushion embodiment, the cushion shape can be cut or stamped from a sheet of uniform thickness material, preferably about ⅛ inch thick. Since many gel cushions can be cut or stamped at the same time, this production method can result in a lower cost, which may be advantageous for single use applications such as in hospitals.

The gel cushion can be cleaned with soap and water, which will restore the tackiness of the material and prolong its usefulness.

Figure 3A:
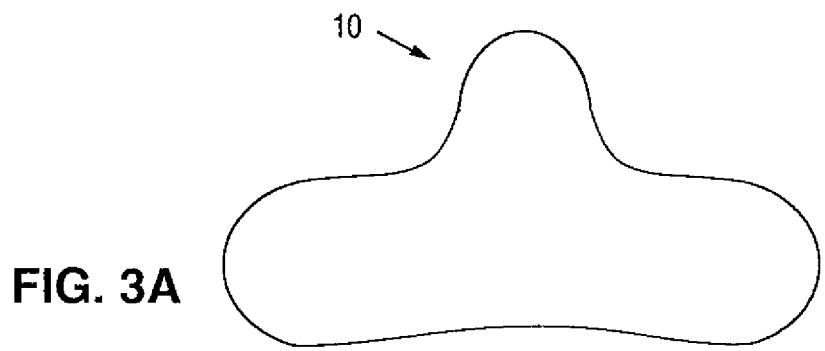
FIGS. 3a-3d are plan views illustrating different sizes of the gel cushion of the present invention.
Figure 3B:
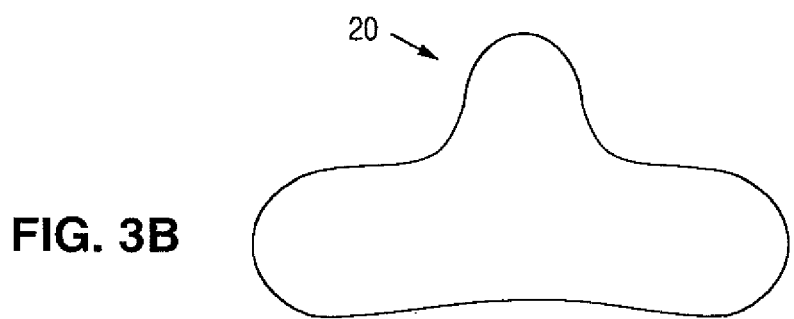
Figure 3C:
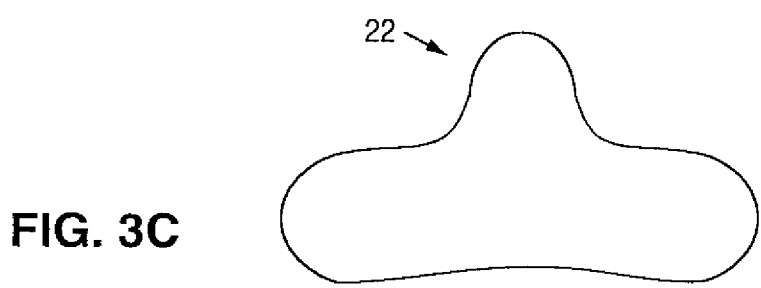
Figure 3D:
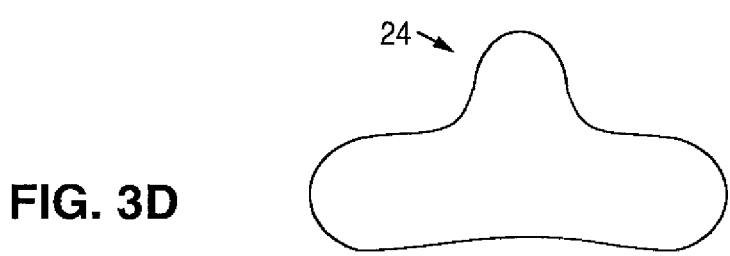

The gel cushion of the present invention may be made in different sizes to accommodate different size faces and for adults, children, and infants. FIGS. 3a-3d illustrate a series of gel cushions. Gel cushion 10, shown in FIG. 3a, is full size, varies in thickness from about 3/16 inch to about ⅛ inch as described above, and is about 4⅛ inches across and about 2 inches high. Gel cushion 20, shown in FIG. 3b, is about 90% of full size, varies in thickness from about 11/64 inch to about 7/64 inch, and is about 3 11/16 inches across and about 1¾ inches high. Gel cushion 22, shown in FIG. 3c, is about 80% of full size, varies in thickness from about 9/64 inch to about 3/32 inch, and is about 3 5/16 inches across and about 1½ inches high. Gel cushion 24, shown in FIG. 3d, is about 75% full size, varies in thickness from about ⅛ inch to about 1/16 inch, and is about 3 inches across and about 1 13/32 inches high. The foregoing are illustrative dimensions and are not intended to limit in any way the scope of the invention.

Figure 4:
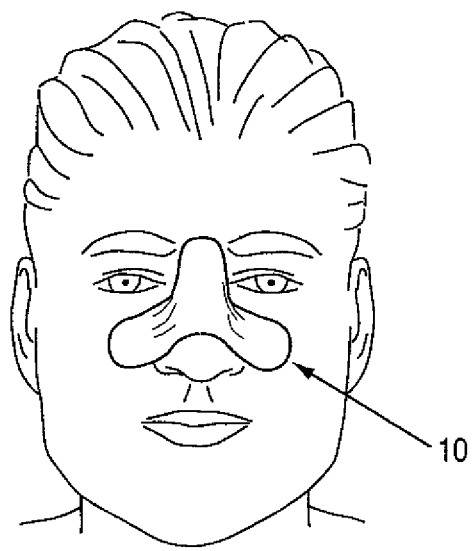
FIG. 4 is a front view of a user with the gel cushion of the present invention placed on his nose bridge.
Figure 5:
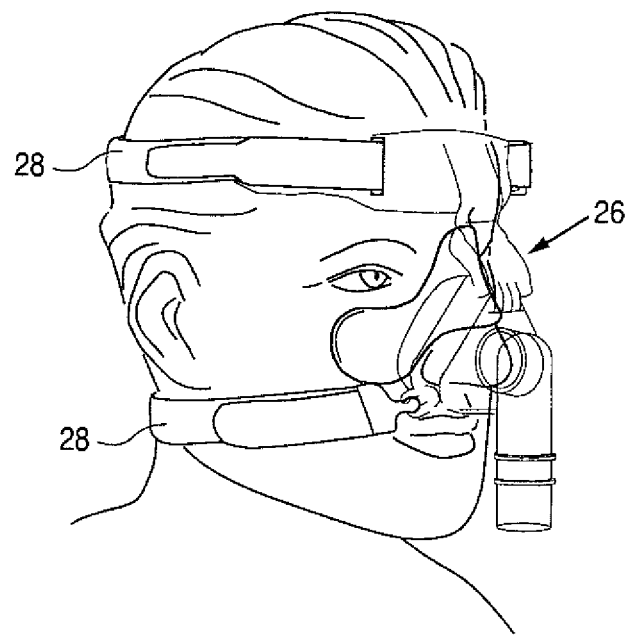
FIG. 5 is a side profile view of the user with the gel cushion and a ventilator mask.

The gel cushion 10 is placed on the nose bridge of a user as shown in FIG. 4. The central lobe 12 is placed on the user's nose bridge, extending upwardly, and the side lobes 14 extend laterally from the nose. A ventilator mask 26 is then placed on top of the gel cushion 10 and straps 28 are arranged to hold the mask in place, as shown in FIG. 5.

The use of the gel cushion according to the present invention significantly improves the comfort of the user of a ventilator mask and enables the effective treatment of sleep apnea. The gel cushion decreases skin breakdown and facial sores that could otherwise be caused by the ventilator mask. The gel cushion improves the overall comfort of both nasal and full face masks. The gel cushion increases user adherence to therapy because the ventilator mask is more comfortable to wear. The gel cushion also decreases leaks between the mask and user's skin, thus making the ventilator mask more effective.

The gel cushion may also be formed in different shapes than the shapes discussed above. For example, the gel cushion may be a rectangle of uniform thickness that can be cut or shaped by the user into a variety of shapes to accommodate the user's needs for a cushion. If the straps of the ventilator mask are causing undue pressure, a piece of the gel cushion can be placed between the user's skin and the straps to solve the problem. For this purpose, another aspect of the invention is packaging a gel cushion of the preferred three-lobe shape along with a rectangular piece of gel material in a sealable box. The gel cushion can be placed in the sealable box between uses and the rectangular piece of gel material is available for use as a cushion in other areas of concern.

From the above description, it will be apparent that the invention disclosed herein provides a novel and advantageous gel cushion for a ventilator mask. The foregoing discussion discloses and describes merely exemplary methods and embodiments of the present invention. As will be understood by those familiar with the art, the invention may be embodied in various other forms without departing from the spirit or essential characteristics thereof. Accordingly, the disclosure of the present invention is intended to be illustrative, but not limiting, of the scope of the invention, which is set forth in the following claims.

The invention claimed is:

1. A cushion pad for a ventilator mask arranged to form a seal with a user's face so as to provide pressurized gas to the user, the cushion pad comprising:
   a first surface adapted to contact the user's face when the cushion pad is positioned on the user's face;
   a second surface opposite the first surface; and
   an edge surface extending from the first surface to the second surface around a perimeter of the cushion pad, wherein
   central portions of the first and second surfaces together form a central region of the cushion pad, the central region being adapted to extend along a central ridge of the user's nose to at least the user's nose bridge when the cushion pad is positioned on the user's nose,
   lateral portions of the first and second surfaces form a pair of side regions of the cushion pad that extend in opposite directions laterally from the central region and are adapted to extend laterally from the user's nose to an area beyond the user's nose when the cushion pad is positioned on the user's nose,
   the cushion pad is adapted to assist the seal in avoiding undue leakage of gas,
   the cushion pad is separate from the ventilator mask,
   a thickness of the central region tapers at a first slope from an upper portion to a lower portion of the central region so that the thickness at the upper portion is greater than the thickness at the lower portion, and
   a portion of the edge surface in the lower portion of the central region tapers from the second surface to the first surface at a second slope that is different from the first slope.

2. A cushion pad as recited in claim 1, wherein a thickness of at least a portion of the central region is greater than a thickness of the pair of side regions.

3. A cushion pad as recited in claim 2, wherein the thickness of the central region tapers toward the side regions.

4. A cushion pad as recited in claim 3, wherein a maximum thickness of the cushion pad is about ⅛ of an inch to about 3/16 of an inch.

5. A cushion pad as recited in claim 4, wherein a minimum thickness of the cushion pad is about 1/16 of an inch to about ⅛ of an inch.

6. A cushion pad as recited in claim 5, wherein a distance between distal ends of the side regions is about 3 inches to about 4⅛ inches.

7. A cushion pad as recited in claim 6, wherein a distance between the upper portion of the central region and the lower portion of the central region is about 1 13/32 inches to about 2 inches.

8. A cushion pad as recited in claim 3, wherein the cushion pad is comprised of a tacky gel material.

9. A cushion pad as recited in claim 8, wherein the tackiness of the gel material is sufficient to maintain the cushion pad on the user's face.

10. A cushion pad as recited in claim 9, wherein the cushion pad comprises a single layer of material.

11. A cushion pad as recited in claim 10, wherein the cushion pad is scented.

12. A cushion pad as recited in claim 1, wherein the portion of the edge surface in the lower portion of the central region forms an acute angle with the first surface and forms an obtuse angle with the second surface.

13. A cushion pad as recited in claim 12, wherein the portion of the edge surface in the lower portion of the central region is positioned to be distal to the user's nose bridge when the cushion pad is placed on the user's nose.

14. A cushion pad as recited in claim 1, wherein the portion of the edge surface in the lower portion of the central region of the cushion pad is angled so that the first surface extends beyond the second surface.

15. A cushion pad as recited in claim 14, wherein the portion of the edge surface in the lower portion of the central region is arranged to avoid undue leakage of gas where the cushion pad ends.

16. A cushion pad as recited in claim 1, wherein the cushion pad is configured to protect a patient's face from damage caused by the ventilator mask being supported against the patient's face.

17. A cushion pad as recited in claim 1, wherein the cushion pad is configured to form a seal with the ventilator mask when the ventilator mask engages the cushion pad.

18. A ventilator mask comprising head straps, wherein the ventilator mask is configured to be sealingly engaged with a cushion pad as recited in claim 11.

19. A ventilator mask as recited in claim 18, wherein the ventilator mask is a continuous positive pressure airway (CPAP) mask.

20. A cushion pad for a ventilator mask arranged to form a seal with a user's face so as to provide pressurized gas to the user, the cushion pad comprising:
a first surface adapted to contact the user's face when the cushion pad is positioned on the user's face;
a second surface opposite the first surface; and
an edge around a perimeter of the cushion pad, the edge connecting the first surface to the second surface, wherein central portions of the first and second surfaces together form a central lobe adapted to extend along a central ridge of the user's nose to at least the user's nose bridge when the cushion pad is positioned on the user's nose,
lateral portions of the first and second surfaces form a pair of side lobes that extend laterally in opposite directions from the central lobe and are adapted to extend laterally from the user's nose to an area beyond the user's nose when the cushion pad is positioned on the user's nose,
the cushion pad is adapted to assist the seal in avoiding undue leakage of gas,
the cushion is substantially T-shaped,
the cushion pad is separate from the ventilator mask,
a thickness of the cushion pad tapers at a first slope from an upper end of the cushion pad to a lower end of the cushion pad so that the thickness of the cushion pad at the upper end of the cushion pad is greater than the thickness of the cushion pad at the lower end of the cushion pad, and
a portion of the edge at the lower end of the cushion pad tapers from the second surface to the first surface at a second slope that is different from the first slope.

21. A cushion pad as recited in claim 20, wherein the portion of the edge at the lower end of the cushion pad is beveled.

22. A cushion pad as recited in claim 21, wherein the portion of the edge at the lower end of the cushion pad is configured so that the first surface extends beyond the second surface.

23. A cushion pad as recited in claim 22, wherein the portion of the edge at the lower end of the cushion pad is positioned to be distal to the user's nose bridge when the cushion pad is placed on the user's nose.

24. A cushion pad as recited in claim 21, wherein the portion of the edge at the lower end of the cushion pad forms an acute angle with the first surface, forms an obtuse angle with the second surface and is adapted to extend from a first side of the user's nose to a second side of the user's nose when the cushion pad is positioned on the user's nose.

25. A cushion pad as recited in claim 21, wherein the portion of the edge at the lower end of the cushion pad is arranged to avoid undue leakage of gas where the cushion pad ends.

26. A cushion pad as recited in claim 20, wherein a thickness of at least a portion of the central lobe is greater than a thickness of the pair of side lobes.

27. A cushion pad as recited in claim 26, wherein the thickness of the cushion pad at the central lobe tapers toward each of said pair of side lobes.

28. A cushion kit for a ventilator mask arranged to form a seal with a user's face so as to provide pressurized gas to the user, in use, the cushion kit comprising:
a first pad separate from the ventilator mask and having a substantially T-shape with a central lobe and two side lobes, the central lobe being adapted to contact the user's face and extend upward from a central ridge of the user's nose to at least the user's nose bridge and the side lobes being adapted to contact the user's face and laterally extend from the user's nose to an area beyond the patient's nose when the first pad is positioned on the user's nose;
a second pad separate from the ventilator mask; and
a sealable container containing both pads,
wherein at least the first pad has a first surface adapted to contact the user's face when the respective pad is positioned on the user's face, a second surface opposite the first surface and a side surface connecting a side edge of the first surface to a side edge of the second surface, wherein the central lobe and the two side lobes of the first pad are formed by the first and second surfaces, wherein at least the first pad is adapted to assist the seal in avoiding undue leakage of gas, wherein a thickness of the first pad tapers at a first slope from an upper portion of the first pad to a lower portion of the first pad so that the thickness of the first pad at the upper portion of the first pad is greater than the thickness at the lower portion of the first pad, and a portion of the side surface at the lower portion of the first pad tapers at a second slope that is different from the first slope.

29. A cushion kit as recited in claim 28, wherein the first pad and the second pad have different shapes.

30. A cushion kit as recited in claim 29, wherein the first and second pads are comprised of a tacky gel, the tackiness of the gel being sufficient to maintain the first and second pads on the user's face.

31. A cushion kit as recited in claim 30, wherein the thickness of the first pad at the central lobe is greater than the thickness of the first pad at the side lobes.

32. A cushion kit as recited in claim 31, wherein the thickness of the central lobe of the first pad tapers toward the side lobes.

33. A cushion kit as recited in claim 30, wherein the first and second pads each comprise a single layer.

34. A cushion kit as recited in claim 28, wherein the portion of the side surface at the lower portion of the first pad is structured so that the first surface extends beyond the second surface.

35. A cushion kit as recited in claim 34, wherein the portion of the side surface at the lower portion of the first pad is positioned to be distal to the user's nose bridge when the first pad is placed on the user's nose.

36. A cushion kit as recited in claim 34, wherein the side surface is arranged to avoid undue leakage of gas where the first pad ends.

37. A cushion kit as recited in claim 28, wherein the portion of the side surface at the lower portion of the first pad is adapted to extend from a first side of the user's nose to a second side of the user's nose when the first pad is positioned on the user's nose.

38. A ventilator mask comprising head straps, the ventilator mask being configured so that when the ventilator mask is mounted on a user's head, a main portion of the ventilator mask is placed on a first cushion pad as recited in claim 28, and the head straps engage a second cushion pad separate from the ventilator mask, the main portion of the ventilator mask is configured to form a seal with the first cushion pad.

39. A ventilator mask as recited in claim 38, wherein the portion of the side surface at the lower portion of the first pad is distal to the user's nose bridge when the first pad is placed on the user's nose, and the ventilator mask is configured so that when the ventilator mask is mounted on the user's head, the ventilator mask forms a chamber and at least a section of the portion of the side surface at the lower portion of the first pad is positioned inside the chamber.

40. A patient interface comprising:
a ventilator mask; and
a cushion pad as recited in claim 1,
wherein the ventilator mask and the cushion pad form a sealed chamber adapted to maintain gas at a predetermined positive pressure.

41. A patient interface as recited in claim 40, wherein the portion of the edge surface in the lower portion of the central region is angled so that the first surface extends beyond the second surface, at least a section of the portion of the edge surface in the lower portion of the central region being adapted to be positioned inside a chamber formed by the ventilator mask when the ventilator mask is positioned on the cushion pad.

42. A patient interface comprising:
a ventilator mask; and
a cushion pad as recited in claim 20,
wherein the ventilator mask forms a chamber adapted to maintain gas at a predetermined positive pressure.

43. A patient interface as recited in claim 42, wherein the portion of the edge at the lower end of the cushion pad is beveled and wherein the at least a section of the portion of the edge at the lower end of the cushion pad is adapted to be positioned inside a chamber formed by the ventilator mask when the ventilator mask is positioned on the cushion pad.

* * * * *